United States Patent [19]
Distler et al.

[11] 3,974,388
[45] Aug. 10, 1976

[54] PATIENTS' SUPPORT INSTALLATION FOR A TOMOGRAPHIC X-RAY APPARATUS

[75] Inventors: Walter Distler; Erich Kintopp, both of Erlangen; Gerhard Linke, Erlangen-Frauenaurach, all of Germany

[73] Assignee: Siemens Aktiengesellschaft, Erlangen, Germany

[22] Filed: Aug. 8, 1975

[21] Appl. No.: 603,114

[30] Foreign Application Priority Data
Aug. 12, 1974 Germany............................ 2438708

[52] U.S. Cl. ............................ 250/445 T; 250/456; 250/491
[51] Int. Cl.² ......................................... G03B 41/16
[58] Field of Search ........ 250/439, 444, 445, 445 T, 250/446, 447, 448, 449, 450, 451, 456, 320, 321, 322, 323, 491

[56] References Cited
UNITED STATES PATENTS

| | | | |
|---|---|---|---|
| 2,659,824 | 11/1953 | Burnham | 250/491 |
| 3,867,634 | 2/1975 | Hounsfield | 250/445 T |

*Primary Examiner*—Craig E. Church
*Attorney, Agent, or Firm*—Haseltine, Lake & Waters

[57] ABSTRACT

A patient's support installation for a transverse axial scanning or tomographic X-ray apparatus utilized for producing tomographic X-ray images, in particular of the skull as a laminagraphic object; consisting of a base or pedestal portion having a frame and a horizontally displaceable table plate which is supported on the latter; a holding arrangement encompassing the laminagraphic object on all sides thereof, fastened to the head end of the table plate, which possesses an aperture into which there is introducible the laminagraphic object to a desired depth; as well as means for fixing the skull in the desired position; and an X-ray transmitter or generator for generating an X-ray beam transilluminating the holding arrangement together with the laminagraphic object at the elevation of the laminagraphic plane, and for scanning the laminagraphic object from different directions in the laminagraphic plane; as well as including an X-ray measuring arrangement which is operatively connected with the X-ray generator and located behind the laminagraphic object in the direction of the beam. The foregoing is inventively attained, in a support installation of the above-mentioned type, by providing a transport web slidingly located on the table plate or pallette so as to be in the longitudinal direction thereof, as the patient support for introduction of the laminagraphic object into the holding arrangement, as well as an adjusting arrangement consisting of a drive means for effecting the displacement of the table plate and the holding arrangement which is coupled therewith with respect to the X-ray beam along the longitudinal direction of the table by specifiable amounts, and finally including an indicating means for the determination of these amounts.

4 Claims, 2 Drawing Figures

PATIENTS' SUPPORT INSTALLATION FOR A TOMOGRAPHIC X-RAY APPARATUS

FIELD OF THE INVENTION

The present invention relates to a patient's support installation for a transverse axial scanning or tomographic X-ray apparatus utilized for producing tomographic X-ray images, in particular of the skull as a laminagraphic object; consisting of a base or pedestal portion having a frame and a horizontally displaceable table plate which is supported on the latter; a holding arrangement encompassing the laminagraphic object on all sides thereof, fastened to the head end of the table plate, which possesses an aperture into which there is introducible the laminagraphic object to a desired depth; as well as means for fixing the skull in the desired position; and an X-ray transmitter or generator for generating an X-ray beam transilluminating the holding arrangement together with the laminagraphic object at the elevation of the laminagraphic plane, and for scanning the laminagraphic object from different directions in the laminagraphic plane; as well as including an X-ray measuring arrangement which is operatively connected with the X-ray generator and located behind the laminagraphic object in the direction of the beam.

DISCUSSION OF THE PRIOR ART

A tomographic X-ray aparatus of the above-mentioned type is described in the publication "The British Journal of Radiology", Volume 46, Number 552; 1973, under the title "Computerized Transverse Axial Scanning" (Tomography): Part I, Description of System, pages 1016 through 1022. The disadvantage of this apparatus, with regard to the introduction of the laminagraphic object into the holding arrangement and the support for the patient, above all consists of in that the patient must be slid across on the table plate or pallette of the support installation for effectuating the introduction of the skull into the holding arrangement, and then must be fixed by a belt band which is tightened over the seat. Moreover, the retention of the patient during the period of the exposure for always about 20 minutes is, due to the belt band, quite unnatural and thereby uncomfortable. This uncomfortable retention, above all, is very significant for accident patients.

SUMMARY OF THE INVENTION

Accordingly, it is an object of the present invention to provide an installation for comfortably supporting a patient in a backrest or reclining position, to introduce him into the holding arrangement without subjecting him to any inherent and external exertions, and to subsequently adjust him precisely with respect to the central beam of the X-ray tube, meaning, that there can be selected the desired layer.

The foregoing is inventively attained, in a support installation of the above-mentioned type, by providing a transport web slidingly located on the table plate or pallette so as to be displaceable in the longitudinal direction thereof, as the patient support for introduction of the laminagraphic object into the holding arrangement, as well as an adjusting arrangement consisting of a drive means for effecting the displacement of the table plate and the holding arrangement which is coupled therewith with respect to the X-ray beam along the longitudinal direction of the table by specifiable amounts, and finally including an indicating means for the determination of these amounts. Thereby is achieved that also extremely restricted patients can be brought from the comfortable rest position into the desired location without any repositioning or displacement with respect to the support.

In order to be able to also bring the patient into the desired position with reference to the central or main beam of the X-ray tube when the holding arrangement is not constituted of a translucent or transparent material, in accordance with a further feature of the invention there is provided, at the table-sided end of the holding arrangement, a light visor which faces towards the patient. In consequence thereof, due to corresponding markings on the laminagraphic object, it becomes possible to bring the desired laminagraphic plane and the radiation plane of the X-ray measuring arrangement into superposition.

In order to facilitate this adjustability and, above all, avoid the need for calculating and measuring procedures, in a further aspect of the invention it is proposed that the indicating means consist of a pointer which is fastened to the table plate and a scale arrangement which longitudinally displaceably is mounted on the base portion, whose length is at least equal to the table stroke and which is formed of two parallel equal divisions of which one possesses values increasing towards the foot-end of the table plate and the other values reducing towards the foot end of the table plate, and the zero points of both divisions being displaced at the head-ended stop of the table plate by the distance between the central beam of the X-ray generator and that of the light visor. Thereby, as is described in greater detail herebelow with reference to the exemplary embodiment, it becomes possible to directly read off the distance of a reference line (eye-ear line) to the desired laminagraphic plane.

In order to render easier the introduction of the laminagraphic object into the holding arrangement, in a further aspect of the invention it is proposed that the transport web is driven by an electromotor and that the holding arrangement, at the end of the aperture which is provided therein for the introduction of the laminagraphic object, is provided with a limit switch arrangement which interrupts the drive of the transport web upon contact by the laminagraphic object, in effect, the patient's skull.

BRIEF DESCRIPTION OF THE DRAWINGS

Reference may now be had to the following detailed description of an exemplary embodiment of the invention, taken in conjunction with the accompanying drawings; in which.

DETAILED DESCRIPTION

Figure 1:
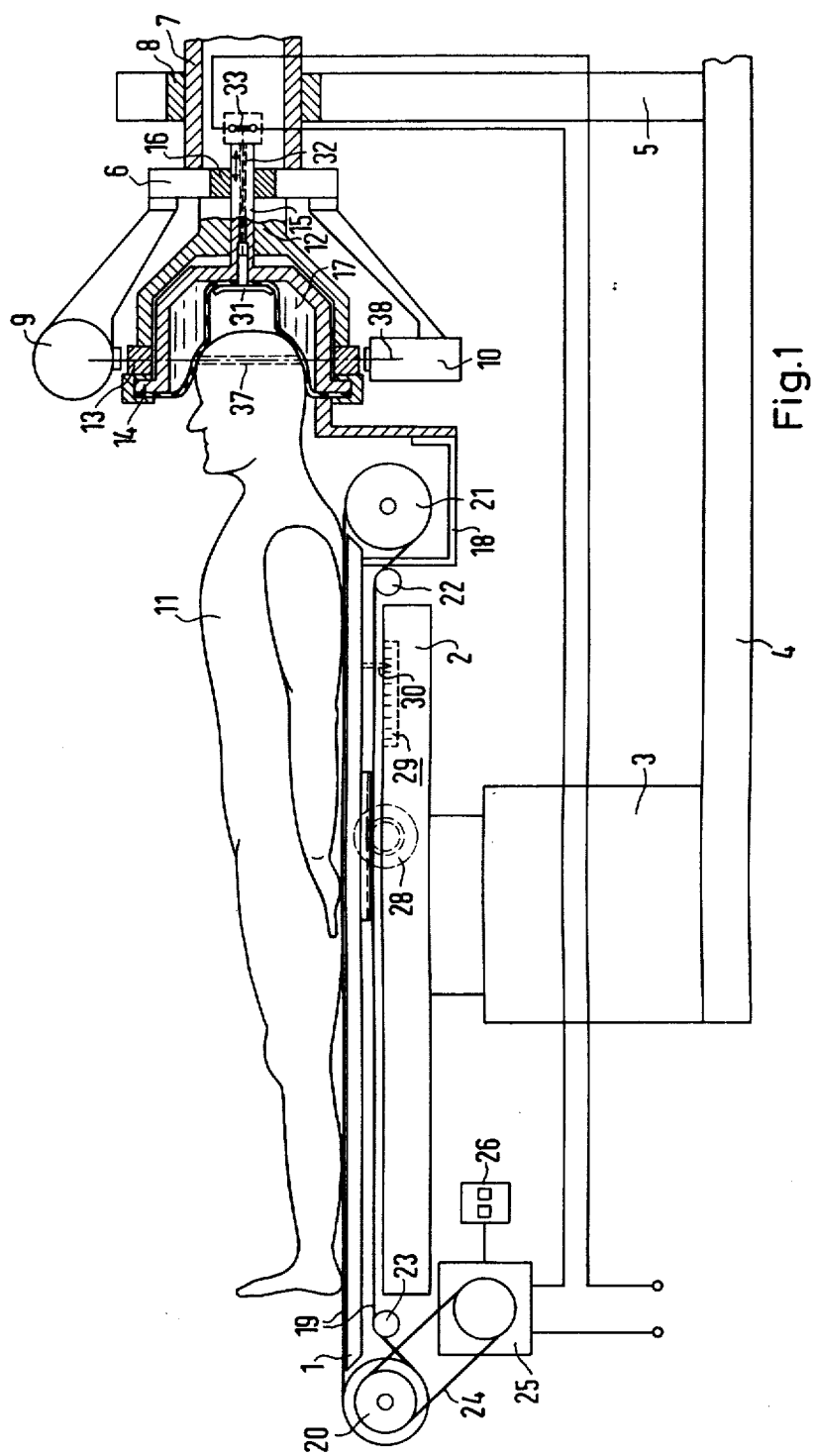
FIG. 1 schematically illustrates, partly in section, a side elevational view of a holding arrangement in a tomographic X-ray apparatus.

The patient support installation illustrated in FIG. 1 consists of a table plate 1 forming a support pallette which is supported on a frame portion 2, through known and thereby not shown means, so as to be longitudinally displaceable. The frame portion 2 rests on a base or pedestal portion 3 which, in turn, is fastened onto a floor plate 4. Positioned on the same floor plate at the head end of the support installation is a column 5, proximate whose upper end a carrier ring 6 is rotatable in a ball bearing 8 through the intermediary of a pivot 7. Located on the periphery of the carrier ring 6 is an X-ray tube 9 and, opposite thereto, an X-ray measuring arrangement 10. Positioned intermediate the X-ray tube 9 and the X-ray measuring arrangement 10 is a holding arrangement for the skull of a patient 11, which forms a laminagraphic object. This holding arrangement is constituted of a holding part 12 fastened to the carrier 6, and which supports a compensating member 13 formed of a rigid plastic material having a tissue-equivalent density. This compensating member possesses a recess in its symmetrical center portion within which there is slidingly inserted a ring member 14 in closely-fitted relationship. This ring member 14 is connected with the carrier ring 6 by means of a pivot 15 and a bearing 16. A hose 17 which may be filled with water is located at the inside of the ring member 14, and through the aid of which there can then be fixed the laminagraphic object after introduction thereof into the ring member 14. The ring member 14 is connected with the table plate 1 through the use of a connecting element 18.

In addition to the foregoing, the patient support installation possesses a conveyor web installation, consisting of an endless transport web or belt 19 which is slidably positioned on the table plate 1 and which envelops the table plate, which is carried by a drive roller 20 at the foot-end of the table plate, a counter-roller 21 at the head-end thereof, as well as reversing rollers 22, 23. The drive roller 20 is driven by means of a gear belt 24 from an electromotor 25. With the aid of a switch arrangement 26, the drive motor 25 may be actuated for rotation in one or the other direction thereof.

Figure 2:
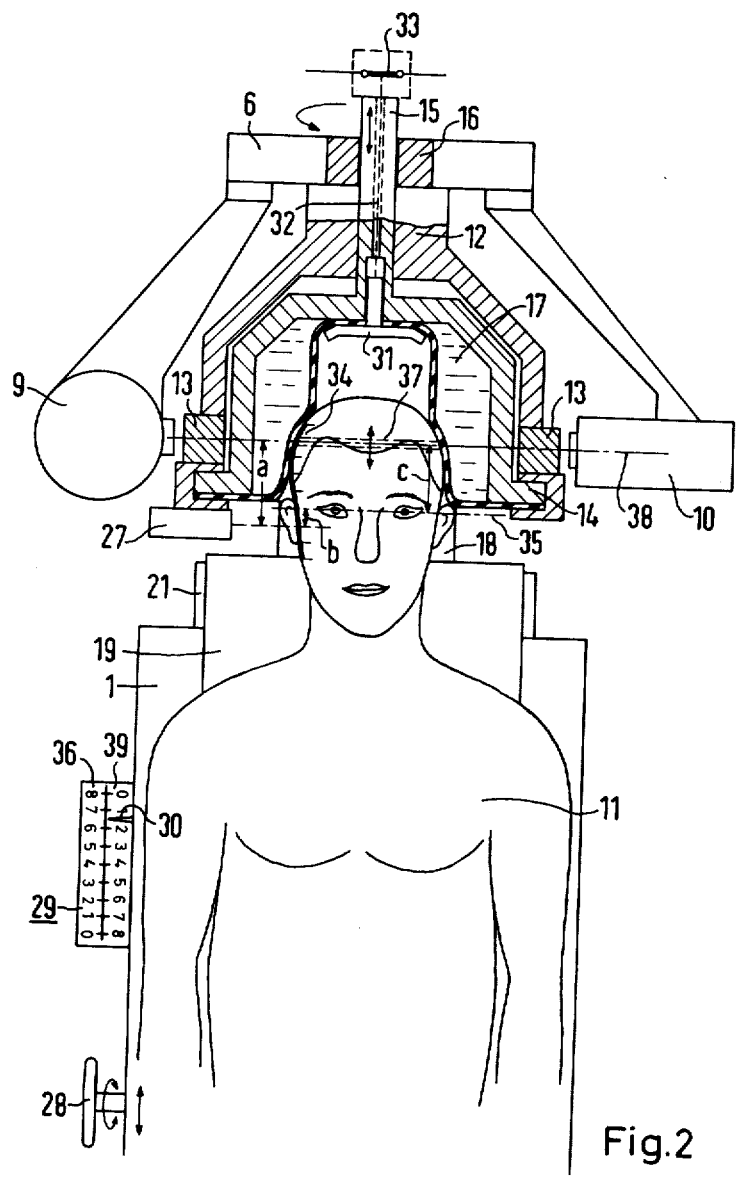
FIG. 2 shows a plan view, partly in section, of the holding arrangement.

As illustrated in FIG. 2 of the drawings, the holding arrangement is shown in section and a portion of the support installation in plan view. Hereby, the elements which are identical with those in FIG. 1 are designated by the same reference numerals. In order to be able to also readily adjust the position of the patient with respect to the central X-ray beam for a holding arrangement constructed of opaque material, a light visor or projector 27 is located on the holding member 12 for the compensating body 13, whose beam is directed against the patient 11. In order to be able to locate the presently selected laminagraphic layer in the plane of the central X-ray beam, there is provided an adjusting installation 28 for the movement of the table plate 1 in the longitudinal direction, as well as a scale arrangement with a longitudinally displaceable scale 29 which is located on the frame 2, and a pointer 30 which is fastened on the table plate or pallette 1, and which traverses over the scale.

The adjustment of the patient is carried out in the following manner:

The patient 11 is initially positioned or laid down on the transport web 19. Then the eye-ear line, which serves as the reference line, is marked on the patient, and an adhesive band which is provided with the same divisions as the scale 29 is adhered to the sides of the facial skull of the patient 11 so that the zero point coincides with eye-ear line, and the adhesive band extends on both sides of this marking, with the positive values in the foot direction and the negative values in the skull direction. Thereafter, the patient is introduced into the opened holding arrangement through actuation of the switch 26 with the aid of the transport web 19 which is moved by means of the drive arrangement or motor 25. Hereby, a cut-off switch arrangement prevents injury to the patient caused by hitting against the ring member 14. For this purpose, the pivot 15 is provided with a longitudinal bore through which there extends a pin 32 provided with a contact plate 31, which pin projects into the ring member and, upon plate 31 contacting the head of the patient 11, actuates a limit switch 33 for deactivating the motor 25. After the completion of the introducing procedure, the water hose 17 is pumped up through an infeed of water by suitable means (not shown) and, as a result, the skull of the patient 11 is fixed within the holding arrangement. The light visor 27 is now switched on through suitable means (not shown) at the head-end position of the table plate 1, and the scale value $b$ is read off as representative of the distance between the location hit by the beam of the light visor and the eye-ear line 35. Through displacement of the two-part scale 29 which possesses two differently designated but in the remainder equal divisions, this value is then brought at its outer division 36 into superposition with the pointer 30. This outer division 36 begins with the value zero and increases towards the head-end of the table plate 1. It indicates the distance $b$ of the central beam of the light visor 27 from the eye-ear line 35. In order to now bring the desired layer 37, whose distance from the eye-ear line is designated by $c$, into coincidence or superposition with the central beam portion 38 of the X-ray beam, there is employed the inner scale division 39. This inner division 39 begins at the place of the zero value of the outer scale division with the value $a_0$ as the distance of the central beam portion of the light visor 27 from that of the X-ray beam 38 at the head-end position of the table plate 1. This value $a_0$ is an apparatus constant and, in the present instance, is about 8 cm. The values of the inner division 39, the introduction of the patient 11, drop to lower values of such magnitude that they constantly indicate the value $c = a - b$, whereby $a$ is the distance between the central beam of the X-ray tube 9 and that of the light visor 27 at the current position of the table plate 1. In order to attain the desired adjustment, it is sufficient to actuate the adjusting arrangement 28 for so long until the pointer 30 indicates the value $c$ on the inner division 39 of the scale 29.

Upon termination of the current tomographic procedure, with the aid of the adjusting arrangement 28 further layers may then be selected in the above-described manner. After the completion of the final layer, the water is removed from the hose 17 so that the latter obtains its maximum opening size, and the patient may then be conveyed out of the holding arrangement with the aid of the transport web 19, through actuation of the switch 26.

While there has been shown what is considered to be the preferred embodiment of the invention, it will be obvious that modifications may be made which come within the scope of the disclosure of the specification.

What is claimed is:

1. In a patient's support installation for a tomographic X-ray apparatus producing tomographic X-ray images, particularly the skull of a patient as a laminagraphic object; including a base member mounting a frame; a table plate being horizontally slidably supported on said frame; a patient holding arrangement being fastened to the head-end of said table plate and adapted to encompass the laminagraphic object on all sides thereof; means for fastening said laminagraphic object in said holding arrangement in a predetermined position; X-ray generator means for generating an X-ray beam transilluminating said holding arrangement and said laminagraphic object at the elevation of the laminagraphic plane, and for scanning the laminagraphic object from different directions in the laminagraphic plane; and X-ray measuring means operatively connected with said X-ray generator means and being positioned behind said laminagraphic object in the direction of said X-ray beam, the improvement comprising: a transport web slidingly supported on said table plate for movement in the longitudinal direction thereof and forming a patient support for introduction of the laminagraphic object into said holding arrangement; an adjusting means for said laminagraphic object including drive means for effecting displacement of said table plate and of said holding arrangement on the longitudinal direction of said table plate with reference to said X-ray beam by specifiable amounts; and indicating means for determination of said displacement amounts.

2. An installation as claimed in claim 1, comprising light visor means directed towards said patient being fastened to the table-sided end of said holding arrangement.

3. An installation as claimed in claim 2, said indicating means comprising a pointer fastened to said table plate, and scale means mounted on said base member being longitudinally displaceable to the extent of the magnitude of the distance to a reference marking on said object, said scale means having a length at least equal to the table plate stroke and including first and second parallel and equal scale divisions, the first of said divisions having values increasing towards the foot end of said table plate and the second of said divisions having values decreasing towards the foot end of said table plate, the zero points of both divisions being offset relative to each other by the distance, at the head-ended contact of said table plate, between the central X-ray beam of said X-ray generator means and the beam of said light visor.

4. An installation as claimed in claim 1, comprising an aperture formed in said holding arrangement for introduction of said laminagraphic object; electromotor means for driving said transport web for conveying said object into said aperture; and limit switch means being located at an end of said aperture for interrupting drive of said transport web upon being contacted by said laminagraphic object.

* * * * *